United States Patent [19]

Neumer

[11] 4,078,934
[45] Mar. 14, 1978

[54] PHOTOSENSITIVE, IMAGE-FORMING COMPOSITION CONTAINING A LEUCO 2,3-DISUBSTITUTED-1-INDANONE AND A PHOTOOXIDANT

[75] Inventor: John Fred Neumer, Hockessin, Del.

[73] Assignee: E. I. Du Pont de Nemours and Company, Wilmington, Del.

[21] Appl. No.: 687,445

[22] Filed: May 18, 1976

Related U.S. Application Data

[62] Division of Ser. No. 139,281, April 30, 1971, Pat. No. 3,992,450.

[51] Int. Cl.$^2$ .................. G03C 1/52; G03C 1/86; G03C 1/78
[52] U.S. Cl. .................. 96/85; 96/87 R; 96/90 R; 96/89
[58] Field of Search .................. 96/90 R, 1.5, 87 R, 96/85; 260/570 R, 490, 471 C, 472, 475 R, 477–479 C, 482 R, 485 J, 571, 576

[56] References Cited
U.S. PATENT DOCUMENTS

| T 896,027 | 3/1972 | Ford et al. ............... | 96/1.5 |
|---|---|---|---|
| 3,445,234 | 5/1969 | Cescon et al. ............ | 96/90 R |

OTHER PUBLICATIONS

Perjessy, et al. "Collection of Czechoslovak Chemical Communications," vol. 35, pp. 3802–3807, (1970).

*Primary Examiner*—Won H. Louie, Jr.

[57] ABSTRACT

Leuco dye compositions containing a compound of the formula:

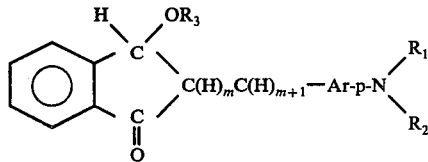

wherein $m = 0$ or 1:
  Ar is an arylene or lower alkyl substituted arylene radical;
  $R_1$ and $R_2$, which may be the same or different, are lower alkyl or hydroxyalkyl groups, or

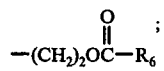

$R_3$ is H, lower alkyl, benzyl, $R_4$, or

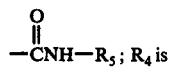

; $R_4$ is

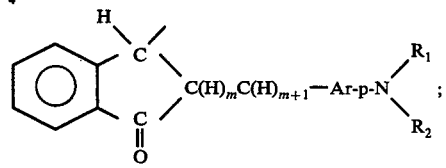

$R_5$ is H, a $C_3$–$C_6$ alkyl group, an aryl group,

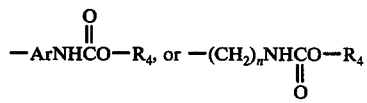

wherein $n = 2$–6; and $R_6$ is a lower alkyl group or an aryl group.

Where $m = 1$, the formula represents a colorless leuco compound; where $m = 0$, the formula represents the yellow dye derivative of the leuco. These compounds are particularly useful in photosensitive compositions.

11 Claims, No Drawings

PHOTOSENSITIVE, IMAGE-FORMING COMPOSITION CONTAINING A LEUCO 2,3-DISUBSTITUTED-1-INDANONE AND A PHOTOOXIDANT

This is a division of application Ser. No. 139,281, filed Apr. 30, 1971, now U.S. Pat. No. 3,992,450.

BACKGROUND OF THE INVENTION

This invention relates to new leuco compounds and the intense yellow dyes obtained therefrom by oxidation. Providing improved new dyes, particularly a new primary (yellow, red and blue) color, is continually an important objective of industrial research. Moreover, the properties required are frequently complicated by the utility envisaged. A particularly challenging task is presented by the demanding set of properties required for colors and color formers to be used in photoimaging systems.

Accordingly, it is an objective of the present invention to provide new compounds which are capable of forming intense yellow images upon oxidation. A further objective is to provide the above compounds which are particularly useful in photosensitive systems. Another objective is to attain superior neutral (gray-to-black) shades, by combining the above novel leuco with selected leuco triarylmethanes which can be oxidized to purple dyes, particularly for use in photoimaging systems.

The invention comprises compounds of the formula:

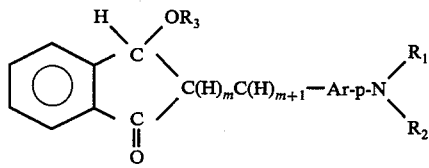

wherein $m = 0$ or 1;

Ar is an arylene or lower alkyl substituted arylene radical;

$R_1$ and $R_2$, which may be the same or different, are lower alkyl or hydroxyalkyl groups, or

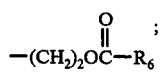

$R_3$ is H, lower alkyl, benzyl, $R_4$, or

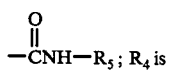

; $R_4$ is

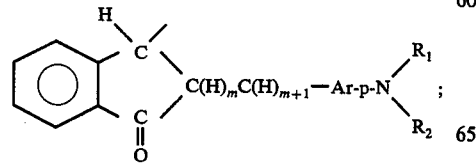

$R_5$ is H, a $C_3$–$C_6$ alkyl group, an aryl group,

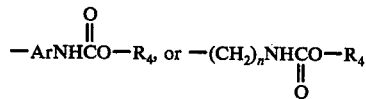

wherein $n = 2$–6; and $R_6$ is a lower alkyl group or an aryl group.

Compounds of the formula, wherein $m = 1$, represent essentially colorless leuco dyes; they may be oxidized to their corresponding yellow dye forms, which are represented by the formula, wherein $m = 0$. The leuco dyes of formula 1 may be used in photosensitive image forming compositions containing a photooxidant capable of oxidizing the leuco dye, such as hexaarylbiimidazoles and N-halolophines. These leuco dyes may also be used in combination with other leucos, such as the preferred leuco triarylmethane of the following general formula:

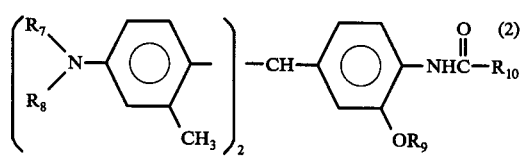

wherein $R_7$, $R_8$, $R_9$, and $R_{10}$, which may be the same or different, are lower alkyl groups. A mixture of leuco dyes of formulas 1 and 2 yields an intense black color on oxidation. Such image-forming compositions may be used to coat paper or film, as hereinafter exemplified, and may contain other ingredients appropriate for such utility, for example, solvents, plasticizers, and binders.

The leuco dyes of formula 1 and their corresponding oxidized dye forms, mixtures thereof with other leuco dyes and their corresponding oxidized dye forms, compositions containing said leuco dyes, oxidized dyes and mixtures thereof, and substrates coated with said compositions, are within the scope of this invention.

DETAILED DESCRIPTION

The leuco dyes of this invention represented by formula 1 wherein $m = 1$, may be oxidized to yellow dyes represented by formula 1 wherein $m = 0$, as exemplified by the conversion of 2-(p-diethylaminophenylmethyl)-3-hydroxy-1-indanone:

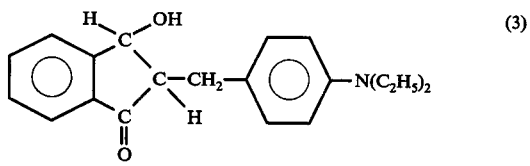

to 2-(p-diethylaminophenylmethylidene)-3-hydroxy-1-indanone:

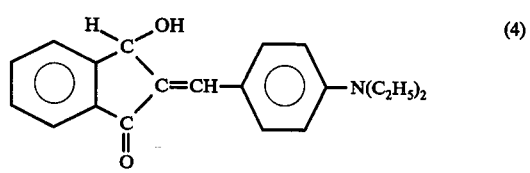

As may be seen from the leuco of formula 2 and the corresponding dye form of formula 4, the carbon atom which connects the indanone and the disubstituted aminoaryl group is bonded to the 2-position of the indanone with a single bond in the leuco and with a double bond in the corresponding dye. This difference is brought about upon oxidation of the leuco, during which two hydrogens are removed from the leuco compound, represented by the general formula 1, wherein $m = 1$, thus forming the double bond and yielding the bright yellow dyes, represented by general formula 1, wherein $m = 0$. The leuco of formula 3 and the dye of formula 4 are preferred species of the compounds of this invention.

Other species include the following compounds and their corresponding dye forms:

2(p-diethylaminophenylmethyl)-3-methoxy-1-indanone,
2(p-dimethylaminophenylmethyl)-3-n-butoxy-1-indanone,
2(p-diethylaminophenylmethyl)-3-n-octyloxy-1-indanone,
2(p-diethylaminophenylmethyl)-3-benzyloxy-1-indanone,
2(p-diethylaminophenylmethyl)-3-nitrobenzyloxy-1-indanone,
2(p-diethylaminophenylmethyl)-1-indanone-3-carbamate,
2(p-diethylaminophenylmethyl)-1-indanone-3-N-n-propylcarbamate,
2(p-diethylaminophenylmethyl)-1-indanone-3-N-phenylcarbamate,
2(p-diethylaminophenylmethyl)-1-indanone-3-N-p-nitrophenylcarbamate, the diurethane of 2(p-diethylaminophenylmethyl)-3-hydroxy-1-indanone and 1,6-diisocyanatohexane, the diurethane of 2(p-diethylaminophenylmethyl)-3-hydroxy-1-indanone and tolylene-2,4-diisocyanate, di[2(p-diethylaminophenylmethyl)-3-indanyl-1-one] ether, 2(p-di-2'-hydroxyethylaminophenylmethyl)-3-hydroxy-1-indanone, 2(p-di-2'-acetoxyethylaminophenylmethyl)-3-hydroxy-1-indanone, 2(p-di-2'-benzoyloxyethylaminophenylmethyl)-3-hydroxy-1-indanone.

The disubstituted aminoaryl groups of the compounds of the invention are preferably diethylaminoaryl such as p-diethylaminophenyl and p-diethylamino-o-tolyl; others operable include p-dimethylaminophenyl, p-N-methyl-N-ethylaminophenyl, p-N-methyl-N-isopropylaminophenyl, p-N-methyl-N-tert-butylaminophenyl, and p-N,N-di-n-butyl-o-tolyl.

The term "lower alkyl" is employed herein to denote an alkyl group having from 1 to 8 carbon atoms. As stated in formula 1, Ar is an arylene radical which may have lower alkyl substituents. Preferably, Ar is an arylene radical having 6 aromatic carbon atoms. The preferred lower alkyl substituent is methyl.

The leuco dyes of this invention may be prepared by condensing 1,3-indandione and the appropriate dialkylaminoarylaldehyde and reducing the intermediate thus formed. Two synthesis methods, leading to a typical leuco of this invention, trans-3-hydroxy-2-(p-diethylaminophenylmethyl)-1-indanone, are outlined below. The first method is most direct in terms of using a minimum number of steps.

METHOD A

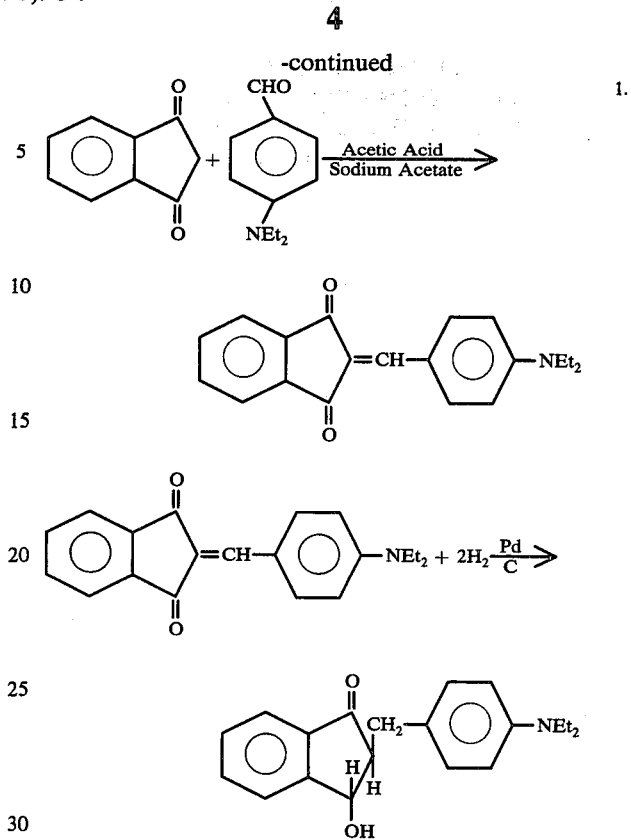

The first reaction of Method A, a condensation, is executed with ease. The second step involves reduction of one ketone group to an alcohol, and saturation of an alkene linkage. Although the desired product is obtained, it may be contaminated with deeply red by-product, thereby requiring a fairly extensive purification procedure giving rise to low yields of product.

A preferred preparative route, of only slightly greater complexity, is outlined below. Using this route, the products of all steps are obtained in sufficient purity to be used without further purification. Moreover, the products of steps 2 and 3 precipitate as readily filterable, easily washable solids; the product of step 1 is not isolated. Finally, the use of aromatic solvents, e.g., benzene, in each step of this preferred route is especially advantageous for obtaining leuco dye in high purity and yield.

METHOD B

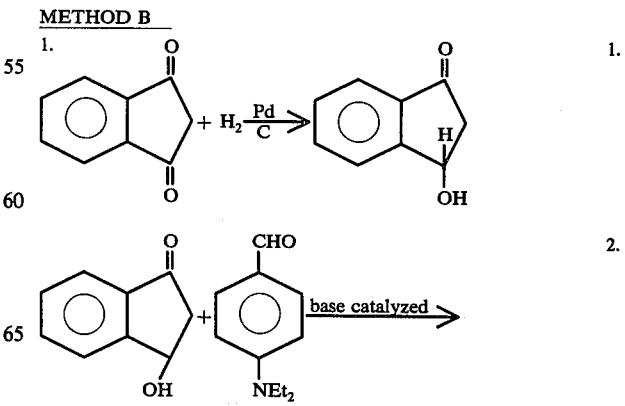

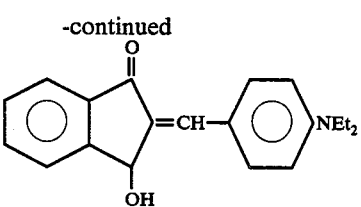

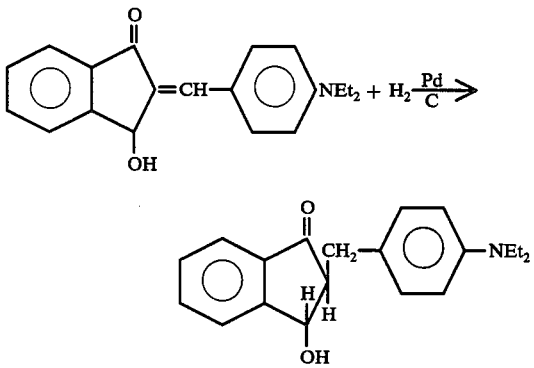

The other leuco compounds of this invention are prepared by an analogous process on substituting the appropriate N,N-disubstitutedaminoarylaldehyde. In addition, urethane leuco dyes may be readily prepared by reacting aryl or alkyl isocyanates with the (secondary) alcohol functional group of the 3-hydroxy-1-indanone leucos by well-known procedures. Thus, the preparation of the urethane derivatives of this invention is readily carried out by reacting the 3-hydroxy-1-indanones with an appropriate aryl or alkyl isocyanate in a suitable inert solvent as, for example, octane or benzene, in the presence of a small amount of a basic catalyst, e.g., pyridine, as shown in Example 8. This synthesis, thus, merely involves dissolving the above reactants in the solvent, heating the reaction mixture for 1–2 hours at 80°–100° C., and then cooling. On cooling, the urethane derivative precipitates in crystalline, easily filtered, readily workable form; the product is isolated in high yield and purity. Further purification may be readily effected by recrystallization; acetonitrile is an effective solvent for recrystallization.

Useful aryl or alkyl isocyanates may vary widely in the number of substituents permissable on the aromatic ring, as well as their position. Preferred aryl isocyanates include phenyl and α-naphthyl isocyanates, o, m-, and p-nitrophenyl isocyanates. Other operable substituents include lower alkyl, lower alkoxy, halo-, and cyano groups. These leuco urethanes yield, when formulated in photosensitive compositions, yellow photoimages of high optical density as shown in Example 8.

The compounds described in this invention are particularly useful in photoimaging applications, wherein the compounds are used in combination with a photooxidant capable of oxidizing the leuco dye so as to form a differently colored compound. The oxidation may be readily effected by photodissociated hexarrylbiimidazoles, as disclosed in U.S. Pat. No. 3,390,994 to Cescon, U.S. Pat. No. 3,390,996 to MacLachlan, and U.S. Pat. No. 3,445,234 to Cescon and Dessauer, whose disclosures are incorporated herein by reference. That is, photolysis of hexaarylbiimidazole compositions containing the above leuco dyes leads to intense yellow images in the exposed area; with a given amount of leuco dye, the density of the color is proportional to the amount of radiation.

Another class of photooxidants useful in photosensitive formulations containing the leuco dyes of this invention, since they are dissociable into the corresponding triarylimidazolyl and halogen radicals, are the N-halotriarylimidazoles (N-halolophines), defined as follows:

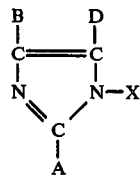

wherein X is Cl or Br; and A, B, and D are aryl groups, which may be the same or different, carbocyclic or heterocyclic, substituent-free or bearing substituents that do not interfere with the dissociation step and the subsequent oxidation of the oxidizable substrate.

The aryl groups include one- and two-ring aryls, such as phenyl, biphenyl, naphthyl, pyridyl, furyl and thienyl. Suitable inert substituents on the aryl groups have Hammett sigma (para) values in the -0.5 to 0.8 range and are other than hydroxyl, sulfhydryl, amino, alkylamino or dialkylamino. Preferably, these inert substituents are free of Zerewitinoff hydrogen, i.e., have no hydrogens reactive towards methyl magnesium iodide. Representative substituents and their sigma values, (relative to H = 0.00), as given by Jaffe, Chem., Rev. 53, 219–233 (1953) arc: methyl (-0.17), ethyl (-0.15), t-butyl (-0.20), phenyl (0.001), butoxy (-0.32), phenoxy (-0.03), fluoro (0.06), chloro (0.23), bromo (0.23), iodo (0.28), methylthio (-0.05), nitro (0.78), ethoxycarbonyl (0.52), and cyano (0.63). The foregoing substituents are preferred; however, other substituents which may be employed include trifluoromethyl (0.55), chloromethyl (0.18), carboxyl (0.27), cyanomethyl (0.01), 2-carboxyethyl (−0.07), and methylsulfonyl (0.73). Thus, the substituents may be halogen, cyano, lower hydrocarbyl (including alkyl, halo alkyl, cyanoalkyl, and aryl), lower alkoxy, aryloxy, lower alkylthio, arylthio, sulfo, alkylsulfonyl, arylsulfonyl, and nitro, and lower alkylcarbonyl. In the foregoing list, alkyl groups referred to there are preferably of 1–6 carbon atoms; while aryl groups referred to therein are preferably of 6–10 carbon atoms.

Preferably the aryl radicals are carbocyclic, particularly phenyl, and the substituents have Hammett sigma values in the range −0.4 to +0.4, particularly lower alkyl, lower alkoxy, chloro, fluoro, bromo and benzo groups.

In a preferred class, the 2 aryl group is a phenyl ring bearing an ortho substituent having a Hammett sigma value in the −0.4 to +0.4 range. Preferred ortho substituents are fluorine, chlorine, bromine, methyl and methoxy groups; especially chloro. Such derivatives tend less than others to form color when the light-sensitive compositions are applied to and dried on substrates at somewhat elevated temperatures, e.g., in the range 70°–100° C.

These N-halotriarylimidazoles are readily prepared by halogenating triarylimidazoles, preferably with N-chlorosuccinimide or N-bromosuccinimide; preparation of triarylimidazoles is old in the art, e.g., see Assignee's U.S. Pat. No. 3,445,234. A convenient preparation involves heating the N-halosuccinimide and triarylimidazole in carbon tetrachloride to reflux temperature for 1–2 hours. Upon cooling to ice bath temperature, succinimide precipitates and is removed by filtration. The desired product (N-halotriarylimidazole) is isolated from the filtrate by removing the solvent; this process may yield an oily residue of product, from which pure, crystalline N-halotriarylimidazole is obtained by recyrstallization from a suitable solvent, e.g., 1-chlorobutane. This general reaction may be depicted as follows:

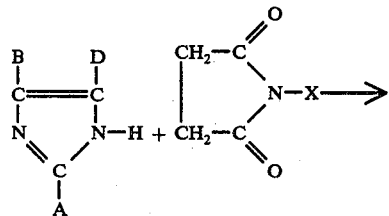

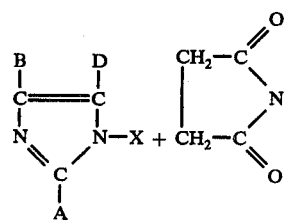

These novel N-halotriarylimidazoles are effective photooxidants for leuco dyes, as described in this invention, since they are photo-dissociable to yield oxidizing agents, presumably as depicted by the following equation:

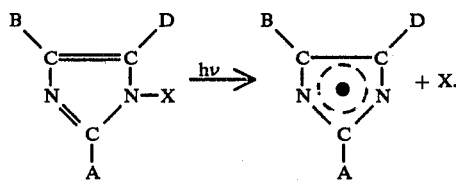

That is, photodissociation of N-halotriarylimidazoles yields both haogen and triarylimidazolyl radicals, both of which are known to oxidize leuco dyes in photosensitive formulations (e.g., U.S. Pat. No. 3,042,515 to Wainer and U.S. Pat. No. 3,445,234).

Preferred N-halotriarylimidazoles include N-chloro-2-(2'-chlorophenyl)-4,5-diphenyl imidazole and N-chloro-2-(2',6'-dichlorophenyl)-4,5-diphenyl imidazole.

Obtaining yellow images, as described herein, with the compounds of this invention is useful in its own right. However, an additional important embodiment of this invention is the combination of the leuco dyes of formula 1, wherein $m = 1$, with selected leuco dyes oxidizable to purple dyes. When oxidized in the preferred hexaarylbiimidazole system, this combination yields very intense (gray-to-black) neutral shades. The preferred companion leuco dyes have a generic structure according to formula 2. A particularly preferred companion leuco dye is 3-methoxy-4-n-octanamidophenyl-bis-(4'-diethylamino-2'-methylphenyl)methane having the following structure:

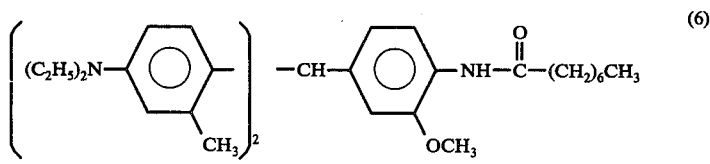

(6)

Upon oxidation, this leuco is converted to a triarylmethane dye of formula:

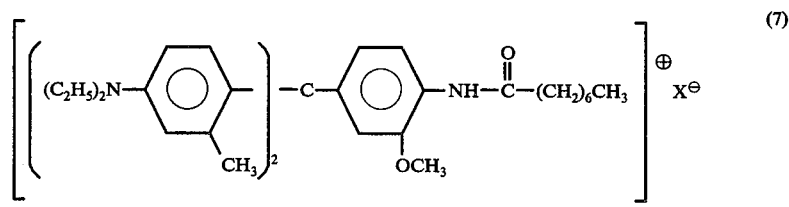

(7)

wherein $X^-$ is the anion of a strong acid.

The compound of formula 7 is, of course, merely a preferred species of the dyes that can be formed by oxidation of the leucos of formula 2. These dyes ae more generally described by the formula:

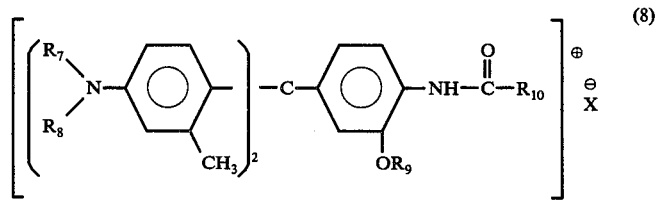

(8)

wherein $X^-$ is the anion of a strong acid, and $R_7$, $R_8$, $R_9$, and $R_{10}$, which may be the same or different, are lower alkyl groups.

Several synthetic routes are available leading to the leuco triarylmethanes. The following equations illustrate a convenient route to a preferred, complementary leuco triarylmethane especially useful for obtaining black photoimages:

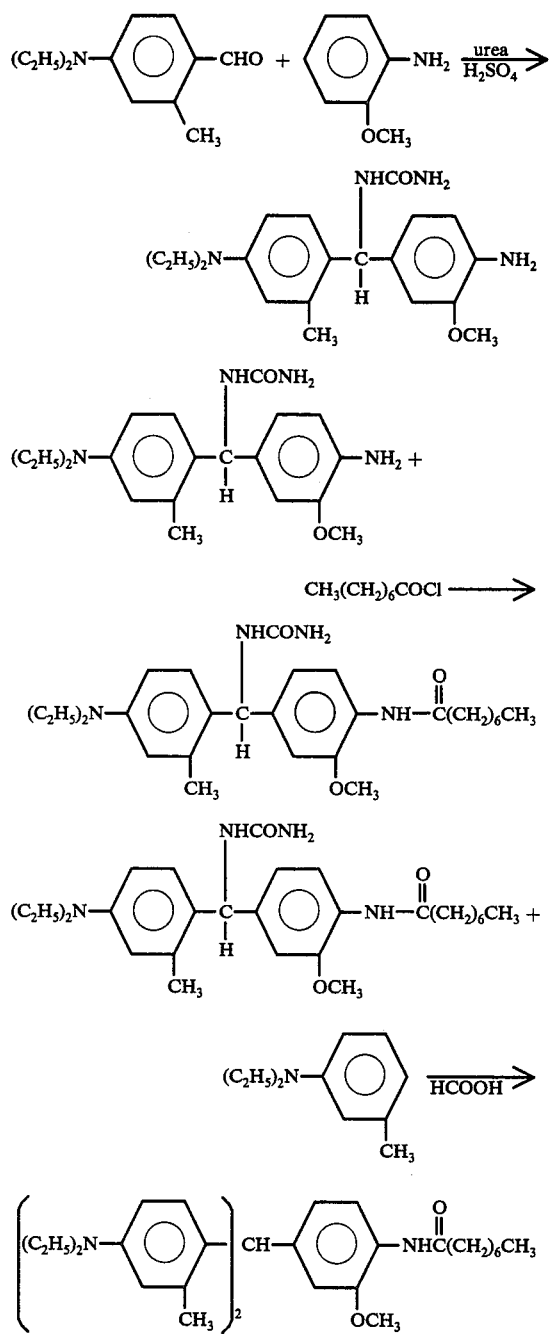

Obviously, related leuco triarylmethanes may be prepared by using different components. For example, the components of steps (1) and (3) may contain the same or different alternate alkyl groups on the nitrogen. The acyl halide of step (2), clearly, could also be varied in chain length or stereochemistry.

In the operation of this embodiment of the invention, i.e., obtaining black images, the above leuco triarylmethanes are also oxidized by photoactivated hexaarylbiimidazoles or N-halophines; the corresponding dye then exists as a cationic triarylmethane having a structure according to formula B. The above X⁻ results from the addition to the photosensitive formulation of a strong acid (as described in U.S. Pat. No. 3,445,234, Col. 13, lines 13-37). Alkylbenzenesulfonic acids, wherein the alkyl group has from 6 to 16 carbon atoms, are preferred. Dodecylbenzenesulfonic acid is particularly preferred.

The following examples provide details regarding preparation and utility of the compounds of the invention.

EXAMPLE 1

A. Preparation of 3-Hydroxy-1-Indanone

A mixture of 73.25 g. (0.5 mole) of 1,3-indandione, 10.0 g. of 10% Pd on charcoal and 800 ml. of 2B-ethanol was added on the 1 liter flask of a Brown Hydrogenator, and hydrogen equivalent to 125 ml. of 1M sodium borohydride solution was added at room temperature and atmospheric pressure (0.5 mole $H_2$). The solution was filtered through a bed of Celite Filter Aid, and the bed washed with ethanol. The ethanol solution was concentrated, and from the concentrate, a small amount of white solid separated, 1,3-indanediol, 1,6 g., m.p. 182°-187°. This by-product was filtered off and discarded. Evaporation of the filtrate gave 70.2 g. of nearly colorless oil (yield > 95%) which can be used directly in the aldehyde condensation. The IR spectrum of the product showed typical hydroxyl and carbonyl absorption.

B. The Preparation of 3-Hydroxy-2-(p-Diethylaminophenyl-methylidene)-1-Indanone A mixture of 56.6 g.(0.32 mole) of p-diethylaminobenzaldehyde, 47.36 g. (0.32 mole) of 3-hydroxy-1-indanone and 7 ml. of piperidine was then heated with magnetic stirring to 80°-100° C. for 1.5 hours (the mixture is a melt at the reaction temperature). The mixture was cooled in ice water, 90 ml. of 1-chlorobutane and seed was added. The product tended to come out as a gum; the solution was therefore heated, cooled (seeded) and muddy brown solid separated. The product was collected by filtration and the brown solid washed until bright orange; 43.62 g. 44% yield, m.p. 139°-141°, m.p. recrystallized material (1-chlorobutane) 142°-143° C. An extra 11% yield was obtained through concentration and refiltration of the filtrate; the latter fraction washed up as cleanly as the first. The IR spectrum and elemental analysis are those expected of the titled merocyanine derivative.

C. Systhesis of Leuco Dye Trans-3-Hydroxy-2-(p-Diethylaminophenyl Methyl) Indanone A mixture of 3.7 g. (0.012 mole) of the recrystallized (m.p. 142°-143°) merocyanine derivative of Part B, 1.0 g. of 10% Pd on charcoal and 200 ml. of absolute ethanol was then added to the hydrogenation flask of a Brown Hydrogenator, and hydrogen equivalent to 15.0 ml. of a 0.2M sodium borohydride solution (0.012 mole of $H_2$) was added at room temperature and atmospheric pressure. At this point, the supernatant solution of the hydrogenation mixture was still colored, and to attain a colorless solution, an additional 4 ml. of borohydride solution was added. The solution was filtered through a bed of Celite, the filtrate was evaporated, and a minimum amount of carbon tetrachloride was added to attain solution at reflux temperature. The solution was cooled in an ice bath and seeded, and an almost colorless solid separated. The solid was collected by filtration and washed with carbon tetrachloride; 1.8 g. (48.5% yield) of pale yellow product was thereby collected, m.p. 113°–115°. The filtrate contained additional product as shown by TLC (Thin Layer Chromatography) analysis; a second solid fraction was crystallized from the filtrate, 0.82 g., m.p. 95°–98°. The latter material would have to be recrystallized before use. The first fraction was of excellent quality and useful without recrystallization. The melting point of the sample recrystallized from methanol, ethanol and acetonitrile was 115°–118° C. The IR spectrum and elemental analyses are those expected of the leuco dye of the invention.

Anal. Calc'd. for $C_{20}H_{23}NO_2$: C, 77.64; H, 7.49; N, 4.53 Found: C, 77.59; H, 7.45; N, 4.55

The product, depicted below, is assigned the trans-structure as shown on the basis that the nmr absorption of $H_A$ is split into a doublet (in $CDCl_3$ containing $D_2O$) with $J_{AB} = 3.0$ cps. The latter small coupling constant is appropriate for only the trans $H_A$ — $H_B$ configuration.

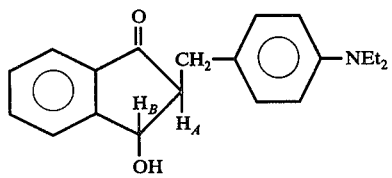

Repeating the above, but using benzene as solvent to the three steps, leads to improved yields. Because $H_A$ is tautomerically labile, and the 2-position to which $H_A$ is attached is a chiral center, cis and trans isomers may exist in equilibrium mixtures, especially in the photoimaging systems described hereinafter.

EXAMPLE 2

Another species of the dye of the invention, 2-(4'-diethylamino-2'-methylphenylmethylidene)-3-hydroxy-1-indanone, gave results similar to the dye of Example 1. This dye has a melting point of 160°–161.5° C. and has the formula:

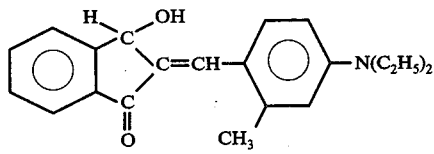

The dye was prepared in 22% yield by condensation of 3-hydroxy-1-indanone with 2-methyl-4-diethylaminobenzaldehyde in the presence of piperidine.

The corresponding leuco dye has a melting point of 112°–114° C. and has the structure:

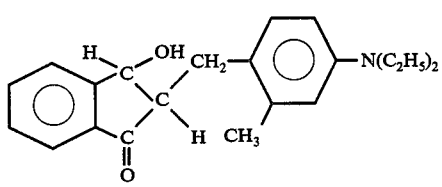

It was prepared from the above dye from in 77% yield by hydrogenation in benzene over Pd on charcoal catalyst.

EXAMPLES 3–5

A coating composition is prepared from the following ingredients:

| | |
|---|---|
| Acetone | 60 ml. |
| 2,2'-Bis(o-chlorophenyl)-4,4',5,5'-tetrakis (m-methoxyphenyl)biimidazole | 0.4180 g. |
| Leuco dye | $1.8 \times 10^{-4}$ mole |
| p-Toluenesulfonic acid monohydrate | 0.400 g. |
| Trimethyl 3,3',3''-nitrilotripropionate | 1.0 ml. |
| 9,10-Phenanthrenequinone | 0.054 g. |
| Cellulose acetate butyrate (Eastman EAB 171-40) | 6.0 g. |
| Polyethyleneoxide adduct of o-phenylphenol average formula $C_6H_5$—$C_6H_4$—$O(CH_2CH_2O)_{2.25}H$ | 3.0 g. |

A high holdout, calendered, bleached, sulfite paper is coated with about 3 milliliters of the above composition per 1000 square centimeters and dried in the air.

Color formation is obtained using a contact printer with Sylvania Blacklight blue fluorescent lamps. Irradiance is 2.75 milliwatts per square centimeter as measured with a YSI Radiometer, Model 65, with probe, Model 6551 in its protective plastic container, against the glass surface of the printer. (The indicated reading, 2.75 mw/cm², is estimated to be about 60% of that actually existing at the surface of the glass.) Samples are exposed for 30 seconds through a $\sqrt{2}$ or a $\sqrt[5]{2}$ stepwedge. The $\sqrt{2}$ stepwedge is vacuum deposited Inconel-X on quartz made by Mufoletto Optical Co. The $\sqrt[5]{2}$ stepwedge is a special stepwedge made by Eastman Kodak Co.

Deactivation is obtained using a printer as above with Sylvania fluorescent lamps containing a special phosphor, PER-105. Irradiance is 5.0 milliwatts per square centimeter measured with the YSI Radiometer as above. The same stepwedges are used as for color formation. Deactivation exposures of 60 seconds through stepwedges are followed by color formation exposure of 30 seconds without stepwedge to determine how much deactivation has occurred.

Three photoimageable/photodeactivatable papers were prepared as above, varying the leuco dyes. One portion of each paper was subjected to imaging irradiation, and another to deactivation irradiation, also as described above. The following table gives the contrast obtainable, using three leuco dyes, between the photoimaged and photodeactivated portions. The contrast is reported as optical density (OD) units, as measured on a MacBeth RD-100 reflecting densitometer. The value ΔOD is the imaged OD minus the deactivated OD. The maximum OD is the visual diffuse optical density obtained on a sample by color formation exposure through step No. 1 (clear area) of the stepwedge.

TABLE I
CONTRAST DATA- YELLOW-IMAGED/DEACTIVATED PAPERS

| Ex. No. | Leuco Dye | OD-Imaged & Deactivated | OD Deactivated | ΔOD |
|---|---|---|---|---|
| 3 | Dye of Example 1 | 0.70 | 0.1 | 0.60 |
| 4 | Dye of Example 2 | 0.62 | 0.1 | 0.52 |
| 5 | 2-(p-Diethylaminophenylmethyl 1-indanone | 0.40 | 0.1 | 0.30 |

Clearly, as evidenced by the data in Table I, the leuco dyes of Examples 1 and 2 are superior (yield more intense yellow images) to the closely related art (Ex. No. 5) under the conditions of these examples. Indeed, nearly a two-fold increase in intensity is obtained with the color formers of this invention. The behavior of the above compounds may, of course, vary in different systems, and no representation is made as to them.

Substantially identical results may be obtained on substituting equivalent weights of the reductant (hydrogen donor) N,N-dibenzylethanolamine acetate for the reductant trimethylnitrilotripropionate. This new reductant is readily prepared by acetylating, N,N-dibenzylethanolamine, which is commercially available, with acetic anhydride in acetic acid as solvent; the preparative details are as follows:

N,N-dibenzylethanolamine, 62.5 g., 0.26 mole, and an equal weight of glacial acetic acid were stirred at room temperature until solution was complete. Following cooling to 10° C., acetic anhydride (53 g., 0.52 mole) was added to effect acetylation. Since acetylation is an exothermic reaction, slow addition and a cooling bath were used to maintain the mixture's temperature at 25° ± 5° C. The reaction mixture was further stirred for 1.5 hours at room temperature upon completing the anhydride addition.

Isolating the product involved first removing the acetic acid solvent by distillation under reduced pressure, while maintaining the pot temperature below 80° C. The pot residue was then neutralized with aqueous sodium carbonate, and extracted with benzene. The benzene phase containing the desired product was washed three times with water and then dried. The benzene was then removed by reduced pressure distillation, maintaining the pot temperature below 60° C. The pot residue gave N,N-dibenzylethanolamine acetate [($C_6H_5$—$CH_2$)$_2$N-$CH_2CH_2OCOCH_3$, 67 g., 92% yield b.p. 334°-336° C., with decomposition] in high yield and sufficient purity to be used as reductant in dual response, photosensitive formulations without further purification. The purity of the product was also confirmed by chromatographic analysis; the infrared and nuclear magnetic resonance spectra were consistent with the structure assigned.

EXAMPLE 6

Preparation of a Preferred Leuco Triarylmethane, 3-Methoxy-4-octanamidophenyl-bis-(4'-diethylamino-2'-methylphenyl) methane A preferred three-step route has been outlined above. The first two steps of the scheme are accomplished with relative ease. Two processes are described for the more difficult step 3; the formic acid condensation method is favored for its ability to yield clean product. The yield in step 3 i.e. the formic acid procedure has been found to depend upon the molar excess of N,N-diethyl-m-toluidine used in the reaction, and therefore three examples of reactions run with varying ratios of reactants are given.

Step 1:

The Preparation of (2-Methyl-4-diethylaminophenyl)-(3'-methoxy-4'-aminophenyl) Methyl Urea A mixture of 96.9 g. (0.792 mole) of o-anisidine, 168.0 g. of urea, 180 ml of water, and 264 g. of conc. sulfuric acid is prepared, with stirring, by addition of the components in rapid succession (in the order given), and 150.3 g (0.792 mole) of 4-diethylamino-o-tolualdehyde (distilled) was added last. The temperature rose without additional heat to reflux temperature (15–20 min.), and, without subsequent heating, the mixture was stirred for a total of 1 hour. The mixture was poured, with mechanical stirring, into a mixture of ice and water (1000 ml), 400 ml of conc. ammonium hydroxide and 800 ml of ether. The resulting heterogeneous mixture was stirred for one-half hour (beaker in ice), the mixture filtered and the cake washed with 1000 ml of water and three times with ether (600 ml each). The crude product, as isolated above, takes the form of irregular size pearls, pale yellow, 280.0 g (96.5% theor.) m.p. 110°-115°. The infrared spectrum is characteristic of the amino urea product.

Step 2:

Acylation of the Amino Urea

To a stirred mixture of 182.7 g (0.5 mole) of amino urea and 1000 ml of acetonitrile was added, at one time, 81.3 g (0.5 mole) of n-octanoyl chloride. The mixture was stirred for 1 hour at room temperature, 2000 ml of water was added to the yellow solution, and 390 ml of 10% sodium carbonate solution was added slowly to allow for gas evolution and crystal formation (the final solution was basic, pH=8). The mixture was filtered, the cake washed with water (3000 ml) and the solid was washed four times with acetonitrile (1300 ml) to give a colorless product, 193.3 g (yield 80% theor.), m.p. 160°-165° C. The infrared spectrum is characteristic of the acylated urea product.

Step 3:

Formation and Separation of the Leuco Dye by the Cellosolve Method

A mixture of 9.65 g (0.02 mole) of the acylated urea product, 3.26 g (0.02 mole) of N,N-diethyl-m-toluidine, 50 ml of Cellosolve and 3 ml of conc. sulfuric acid was mixed in the order noted, and a solid separated after a 3-4 min. period which dissolved upon heating to reflux temperature (134° C.). The stirred mixture was heated at reflux temperature for 40 min., and 50 ml of isopropanol was added. The addition of sodium carbonate solution (to pH=9) caused a dispersed tan gum to separate; the addition of 25 ml of methanol, with stirring of the neutralized mixture in an ice bath, gave a filterable solid. The latter was collected by filtration and washed with isopropanol, water, and 2B-ethanol, yielding 5.9 g of leuco dye, m.p. 85°-87° C. The infrared spectrum is characteristic of 3-methoxy-4-octanamidophenyl-bis-(4'-diethylamino-2'-methylphenyl)methane. A second fraction (1.0 g.) was collected from the filtrate for a total collected yield of 53%. The melting point of the sample recrystallized from methanol was 86°-89° C.

Anal. Calc'd. for $C_{38}H_{55}N_3O_2$: C, 77.90; H, 9.46; N, 7.17.

Found: C, 77.87; H, 9.67; N, 7.68.

Alternative Step 3:

Condensation in Formic Acid

A mixture of 9.65 g. (0.02 mole) of the acylated urea product, 9.78 g (0.06 mole) of N,N-diethyl-m-toluidine and 25 ml of formic acid was heated at reflux temperature for one-half hour, cooled and poured in 50 ml of conc. ammonium hydroxide solution and ice water. The oil which separated was separated from the aqueous phase with methylene chloride, and both methylene chloride and some excess toluidine were removed by distillation of 500 ml of added water on a rotary evaporator. The water insoluble residue was triturated with ethanol to give a colorless solid, m.p. 88°-90°, 5.00 g of leuco dye. The filtrates from above were treated by conventional steam distillation techniques (because of remaining toluidine), and water insoluble residue, when treated as above, yielded 3.2 g of colorless leuco dye. The latter fraction possessed a minor leuco dye contaminant (as determined by TLC), yet the two fractions possessed identical infrared spectra (total yield, 71%). The infrared spectrum is characteristic of 3-methoxy-4-octanamidophenyl-bis-(4'-diethylamino-2'-methylphenyl) methane.

The reaction of 0.02 mole of acylated urea and 0.04 mole of N,N-diethyl-m-toluidine, when treated as above, gave a 65% yield of leuco dye.

A third example of the formic acid condensation is as follows:

A mixture of 38.60 g (0.08 mole) of the acylated urea, 13.04 g (0.08 mole) of N,N-diethyl-m-toluidine and 100 ml of formic acid was heated at reflux temperature for 150 min., cooled, and poured into a mixture of 100 ml of isopropanol, 100 ml of water, 230 ml of conc. ammonium hydroxide solution, and 8.0 g of the leuco dye used as seed. A mixture of brown gum and solid separated in one lump, the aqueous phase was decanted, and a mixture of 100 ml of methanol and 75 ml of isopropanol was added to the residue. Heating nearly dissolved the solid phase, and cooling gave a thick crystalline slurry; the product was collected by filtration and washed to a colorless state with isopropanol; 28.9 g leuco dye was collected, yield corrected for seed, 20.90 g (45% yield).

EXAMPLE 7

A Black, Photoimageable/Photodeactivatable-Proof Paper

A coating composition is prepared from the following ingredients:

| Moles | Weight (Grams) | Wt. Percent | Constituent |
|---|---|---|---|
| | 237 g (300 ml) | 80.37 | Acetone |
| $3.2 \times 10^{-3}$ | 2.50 | 0.85 | 2,2-(o-chlorophenyl)-4,4',5'-tetrakis (m-methoxyphenyl)-biimidazole |
| $1.35 \times 10^{-2}$ | 4.20 | 1.42 | Richonic Acid B (Richardson Co. tradename for dodecylbenzenesulfonic acid) |
| $8 \times 10^{-3}$ | 2.2 | 0.74 | triethanolamine triacetate |
| $1.2 \times 10^{-2}$ | 3.3 | 1.12 | trimethyl 3,3',3"-nitrilotripropionate |
| $1.17 \times 10^{-3}$ | 0.2430 | 0.082 | 9,10-phenanthranequinone |
| | 30.0 | 10.16 | cellulose acetate butyrate (thermoplastic binder, Eastman EAB 272-20) |
| $6.5 \times 10^{-5}$ | 0.015 | 0.005 | pyrenequinone (a 1:1 mixture of 1,6- and 1,8-isomers) |
| | 6.50 | 2.20 | Santicizer-3 (N-ethyl-p-toluenesulfonamide, Monsanto Chemical Company) |
| | 5.70 | 1.93 | polyethyleneoxide adduct of o-phenylphenol prepared from 2.25 moles of ethylene oxide per mole of the phenol and having the average formula $C_6H_5-C_6H_4-O(CH_2CH_2)_{2.25}H$ |
| | 2.0 | 0.68 | "Syloid" 63 - a 9 micron synthetic silica produced by Grace-Davidson Chemical Co. |
| | 0.25 | 0.085 | mixed fluorocarbon esters of formula $F(CF_2CF_2)_nCH_2CH_2OCO-(CH_2)_{16}CH_3$ where n = 3 and 4 |
| $1.08 \times 10^{-3}$ | 0.330 | 0.11 | trans-3-hydroxy-2-(p-diethylaminophenyl-methyl)-1-indanone |
| $1.08 \times 10^{-3}$ | 0.6320 | 0.21 | 3-methoxy-4-n-octanamidophenyl-bis-(4'-diethylamino-2'-methylphenyl) methane |

The above formulation was coated on regular HG paper, a commercial product of the P. J. Schweitzer Co. Following drying, to evaporate the volatile solvent, the coating weight of the dried coating was 11 lbs./3000 square feet. This coated paper, upon irradiation with ultraviolet light, gave a black photoimage with good contrast as described in the following table:

| SENSITOMETRY RESULTS | | | |
|---|---|---|---|
| | Initial | 2 weeks | 4 weeks |
| Optical Density (Imaging) | 1.03 | 1.02 | 1.02 |
| Background Optical Density (Deactivation) | 0.13 | 0.12 | 0.12 |

The imaging and deactivation light sources were the same as described for Examples 3-5.

EXAMPLE 8

Urethane Derivatives

Urethane derivatives of the leuco dye prepared in Example 1 were prepared according to the following general equation:

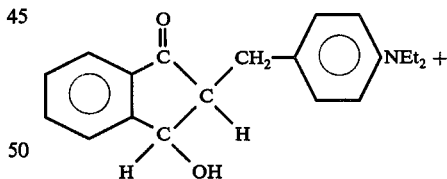

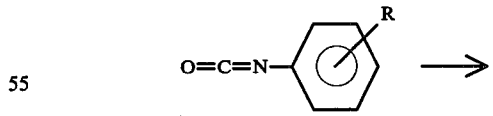

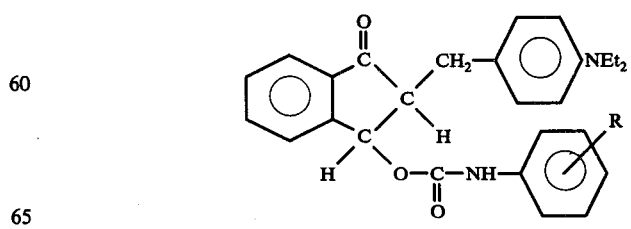

The derivatives prepared had the following structures:

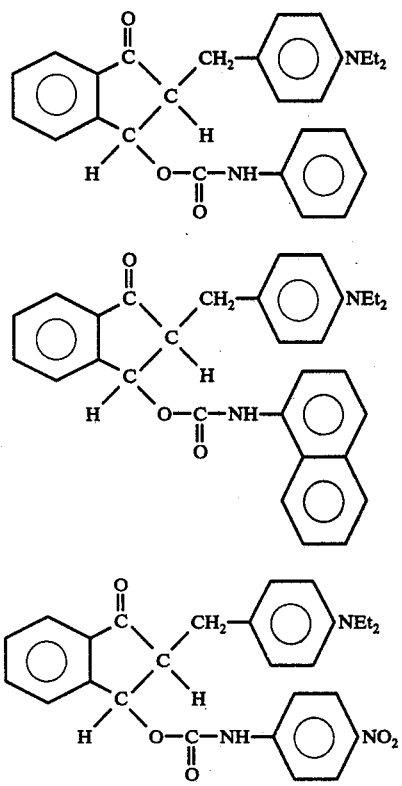

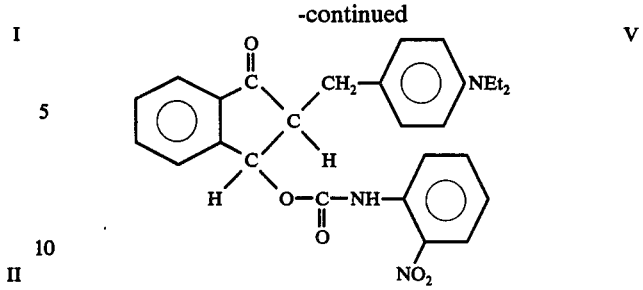

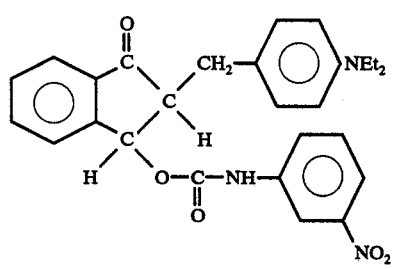

Preparation of I

The leuco yellow dye of Example 1 (1 g., 0.03 mole), phenyl isocyanate (0.5 g.) and octane (5 ml.) was heated to reflux. When the temperature reached 100° C., pyridine (3 drops) was added. The solids immediately went into solution; after 1.5 hours at 100° C., thin layer chromatographic (tlc) analysis showed that all the original yellow color former (of Example 1) had reacted and a new yellow color former was produced. On cooling, the product (I) which precipitated was collected by filtration. After recrystallization from acetonitrile, the m.p. was 170°–171.5° C.

Anal. Calc'd. for $C_{27}H_{28}N_2O_3$ (Formula I): C, 75.67; H, 6.57; O, 11.20; N, 6.54. Found: C, 75.56; H, 6.64; O, 11.28; N, 6.44.

Products II–V were prepared similarly; the results are reported in the following table:

TABLE

| Urethane Derivative | Amount Leuco of Example 1 | Aryl Isocyanate and (amount) | Solvent and (amount) | Reaction Time (hrs.) | Melting Point of Derivative |
|---|---|---|---|---|---|
| II | 2 g. (0.0065 mole) | α-naphthylisocyanate (1.1 g., 0.0065 mole) | octane (20 ml.) | 1.5 hrs. at 100° C. | 128–129° C. |
| III | " | p-nitrophenyl isocyanate (1.1 g., 0.0065 mole) | benzene (20 ml.) | 1 hr. at reflux | 169–170° C. |
| IV | " | m-nitrophenyl isocyanate (1.1 g., 0.0065 mole) | " | 2 hrs. at reflux | 164–166° C. |
| V | " | o-nitrophenyl isocyanate (1.1 g., 0.0065 mole) | " | " | 135–136° C. |

Photooxidation Using Urethane Derivatives I, III–V Color Formers

A coating composition is prepared from the following ingredients:

| | |
|---|---|
| Acetone | 60 ml. |
| 2,2'-Bis(o-chlorophenyl)-4,4',5,5'-tetrakis (m-methoxyphenyl)biimidazole | 0.64 g. |
| Leuco dye | $6 \times 10^{-4}$ mole |
| p-Toluenesulfonic acid monohydrate | 0.2283 g. |
| Cellulose acetate butyrate (Eastman EAB 531-1) | 6.0 g. |
| Polyethyleneoxide adduct of o-phenylphenol average formula $C_6H_5$—$C_6H_4$—$O(CH_2CH_2O)_{2.25}H$ | 4.0 g. |

The above formulations were applied to Mylar ® polyester film (7 × 8 inches) to yield a dry coating weight (after drying to remove the volatile solvent) of approximately 0.6 g./56 in.² The dry, coated films were imaged by exposing the films for 30 seconds, as described in Examples 3-5, to Sylvania Blacklight Blue fluorescent lamps. Using the Cary spectrophotometer, the μmax, and optical densities of the imaged samples were measured (Table II). The data collected from this experiment showed that two of the four compounds have optical densities, after imaging for 30 seconds, that are greater by a factor of at least 1.6 when compared to Example 1. Compound I has an optical density that is greater by a factor of 2 (1.50 compared to 0.76) and compound V has an optical density that is greater by a factor 1.6 (1.22 compared to 0.76). The data are summarized in Table II below:

TABLE II

| Amount | Color Former | OD after Imaging for 30 sec. |
|---|---|---|
| 0.185 g. | Example 1 | 0.76 |
| 0.257 g. | Compound I | 1.50 |
| 0.284 g. | Compound III | 0.88 |
| 0.284 g. | Compound IV | 0.79 |
| 0.284 g. | Compound V | 1.22 |

The imaging was performed as in Examples 3-5, and optical density was measured with a Cary spectrophotometer at μmax., which was determined to be 445 nm. The optical density of the background (unimaged formulation) was in all cases less than 0.08.

EXAMPLE 9

Preparation of N-Halotriarvlimidazoles

A.

N-Chloro-2-(2'-chlorophenyl)-4,5-diphenylimidazole

The preparation of 2-(o-chlorophenyl)-4,5-diphenylimidazole (o-chlorolophine) is described in British patent specification No. 997,396, Example 1.

A mixture of 14.24 g. of 2-(o-chlorophenyl)-4,5-diphenylimidazole (0.04 mole), 5.34 g. of N-chlorosuccinimide (0.04 mole), and 500 ml. of carbon tetrachloride was heated at reflux temperature for 1 hour, cooled to 0° C., and the precipitated residue was separated by filtration. The solvent of the filtrate was evaporated under vacuum at 35° C. 1-Chlorobutane was added in minimal amount to the oily residue to induce crystallization. The solid that formed was collected by filtration; 5.88 g., m.p. 105°-107° C. An additional fraction was collected from the filtrate, 5.45 g.

Anal. Calc'd. for $C_{21}H_{14}N_2Cl_2$: C, 69.06; H, 3.86; N, 7.67; Cl, 19.41. Found: C, 68.66; H, 3.68; N, 7.74 Cl, 19.39.

Infrared and nuclear magnetic resonance spectra are consistent with the tilted compound's structure.

B. N-Bromo-2-(2'-chlorophenyl)-4,5-diphenylimidazole

A mixture of 6.62 g. (0.02 mole) of o-chlorolophine 3.56 g. (0.02 mole) of N-bromosuccinimide, and 200 ml. of carbon tetrachloride was heated at reflux temperature for 1 hour. During this time the solution became pale orange. The solution was cooled to 0° C., filtered, and the succinimide washed with carbon tetrachloride; weight, 2.16 g. The filtrate was concentrated to oil under vacuum at 35° C. The orange residue was diluted with 15 ml. of 1-chlorobutane and stirred magnetically. The stirring induced crystal formation. A tan-orange solid separated, was filtered, washed with cold 1-chlorobutane, and collected by filtration; 5.192 g.; the IR spectrum was almost identical with that of the chloro derivative A; m.p. 103°-105° C.

Anal. Calc'd. for $C_{22}H_{14}N_2ClBr$: C, 61.56; H, 3.44; N, 6.84. Found: C, 61.73; H, 3.53; N, 6.88.

The infrared and nuclear magnetic resonance spectra were also consistent with a structure corresponding to the tilted compound.

C.

N-Chloro-2-(2',6'-dichlorophenyl)-4,5-diphenylimidazole 2-(2',6'-Dichlorophenyl)-4,5-diphenylimidazole was prepared in a manner identical with Example II of Brit. patent specification No. 997,396, but substituting 2,6-dichlorobenzaldehyde for the 2,4-dichlorobenzaldehyde of the Example.

A mixture of 14.60 g. (0.04 mole) of the 2-(2',6'-dichlorophenyl)-4,5-diphenylimidazole, 5.34 g. (0.04 mole) of N-chlorosuccinimide, and 400 ml of carbon tetrachloride was heated at reflux temperature for 2 hours. The solution was cooled, filtered, and the filtrate concentrated under vacuum. The resulting solid-oil mixture was triturated with 1-chlorobutane to give a residue of 16.68 g., m.p. 120°-140° C. (broad). The compound proved difficult to recrystallize from common solvent and only acetonitrile and nitromethane afforded resonable recovery of crystals; from the latter solvents the crystals formed as large chunky aggregates. The best fraction 0.7664 g. has m.p. 125°-127° C.; an IR spectrum showed no NH absorption and a very strong 1620 cm$^{-1}$ band.

Anal. Calc'd. for $C_{22}H_{13}N_2Cl_3$: C, 63.10; H, 3.28; N, 7.01; Cl, 26.61. Found: C, 63.32; H, 3.37; N, 7.38; Cl, 26.20.

The infrared and nuclear magnetic resonance spectra were all consistent with the structure of the tilted compound.

Use of N-Halotriarylimidazoles as Photooxidants for Leuco Dyes

Two solutions were prepared. Solution A contained the leuco dye of Example 1 (0.5 g.) in benzene (100 ml.); solution B contained N-chlorolophine as prepared in Example 9, Part A, (0.01 g.) in benzene (2 ml.). A 1.00 ml. aliquot of solutions A and B were mixed, and the resulting solution applied totally to 64 cm.$^2$ of Whatman No. 1 filter paper. The paper was dried in an air stream and then a portion was irradiated with a Xenon (HiCo) flash lamp to give a strong yellow image over a nearly colorless background.

Substantially identical results may be obtained with N-bromolophine of Part B and N-chlorolophine of Part C.

EXAMPLE 10

Leuco Yellow Imaging, Photopolymerization Fixing

Through exposure control, e.g., by altering the intensity and time of exposure, as more fully described in Cescon, Cohen & Dessauer, U.S. application Ser. No. 740,130, filed June 26, 1968, and assigned to the assignee herein, color-forming and polymerization reactions can be controlled so as to produce substantially colored or uncolored compositions. Thus polymerization fixed images can be produced in imaging applications by sequentially applied exposures that substantially completely polymerize the composition while controlling the amount of color produced in adjacent areas.

The leuco dyes of this invention are also useful in this type of photosensitive formulation, as detailed below.

A coating composition was prepared as follows:

| | |
|---|---|
| Acetone | 45.6 ml. |
| Cellulose acetate butyrate (EAB-272-20) | 3.96 g. |
| Triethyleneglycol dimethacrylate | 3.96 g. |
| 2,2'-Bis(o-chlorophenyl)-4,4',5,5'-tetrakis-(m-methoxyphenyl)biimidazole | 0.471 g. |
| 2,2'-Bis(o-chlorophenyl)-4,4',5,5'-tetraphenylbiimidazole | 0.471 g. |
| Leuco dye of Example 1 | 0.309 g. |
| p-Toluenesulfonic acid | 0.375 g. |
| 2-Mercaptobenzoxazole | 0.014 g. |

These formulations were coated on 3 mil Mylar ® polyester film, dried and laminated with a 1.42 mil Mylar ® polyester film. The dried coating weight was equivalent to 0.36 lb./100 ft.$^2$; the dried coating thickness was approximately 0.6 mil.

The above coated film was imagewise deactivated (by irradiation through a stencil or master) by a 12-second exposure (0.9 mw/cm.$^2$) to low intensity radiation from a high pressure mercury-vapor lamp (HBO-200), which had been passed through a water, a Corning I-69, and a Schott UG-11 filter combination; this filter combination transmits light principally in the near ultraviolet range.

The resulting deactivated film was then thoroughly dried by storage in a desiccator (over "Drierite") for 3.5 hours. The resultant, deactivated (photopolymerized), dry film was then imaged by exposure to 5 flashes (high intensity) from a Xenon flashtube (Model K, HiCo Corporation, Watertown, Mass.).

The sensitometry results obtained are reported below. The numbers are the optical densities obtained in the yellow region of the spectrum, as measured by a Cary spectrophotometer at 443 nm.

| OPTICAL DENSITIES | | |
|---|---|---|
| Imaged and Deactivated | Deactivated Only | ΔO.D. |
| 2.00 | 0.20 | 1.80 |

I claim:

1. A photosensitive, image-forming composition containing a leuco dye of a compound (1) of the general formula:

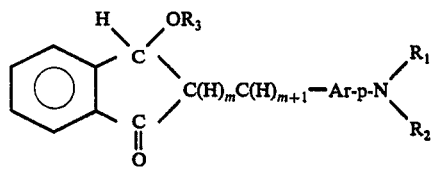

wherein $m = 1$;

Ar is an arylene or lower alkyl substituted arylene radical;

$R_1$ and $R_2$, which may be the same or different, are lower alkyl or hydroxyalkyl groups, or $$-(CH_2)_2OC-R_6; \quad R_3 \text{ is H, lower alkyl, benzyl, or } -CNH-R_5;$$

$R_5$ is H, a $C_3$-$C_6$ alkyl group, an aryl group,

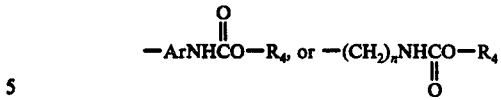

wherein $n = 2$-$6$ and $R_4$ is

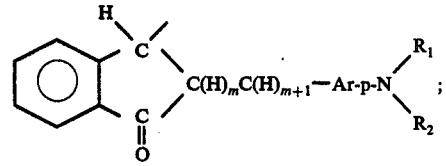

and $R_6$ is a lower alkyl group or an aryl group, and a photooxidant capable of oxidizing the leuco dye.

2. An article comprising an inert substrate coated with a composition of claim 1.

3. The coated article of claim 2 wherein the substrate is paper.

4. The coated article of claim 2 wherein the substrate is a film.

5. The composition of claim 1 wherein said photooxidant is selected from the group consisting of hexaarylbiimidazoles and N-halotriarylimidazoles.

6. A photosensitive, image-forming composition containing a leuco dye mixture of a compound (1) of the general formula:

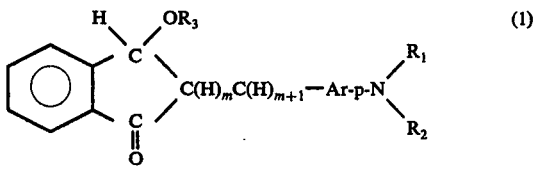

wherein $m = 1$;

Ar is an arylene or lower alkyl substituted arylene radical;

$R_1$ and $R_2$, which may be the same or different, are lower alkyl or hydroxyalkyl groups, or $-(CH_2)_2OC-R_6$; $R_3$ is H, lower alkyl, benzyl, or $-CNH-R_5$;

$R_5$ is H, a $C_3$-$C_6$ alkyl group, an aryl group,

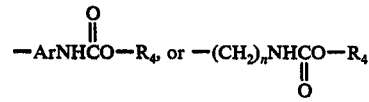

wherein $n = 2$-$6$ and $R_4$ is

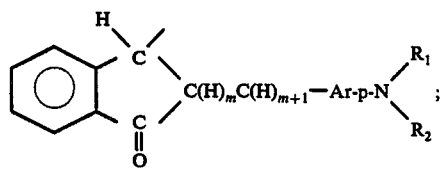

and $R_6$ is a lower alkyl group or an aryl group, and a triarylmethane compound (2) having the formula

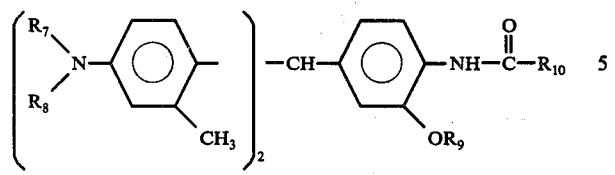

wherein $R_7$, $R_8$, $R_9$, and $R_{10}$, which may be the same or different, are lower alkyl groups, and a photooxidant capable of oxidizing the leuco dye.

7. The photosensitive, image-forming composition mixture of claim 6 wherein said triarylmethane compound has the formula

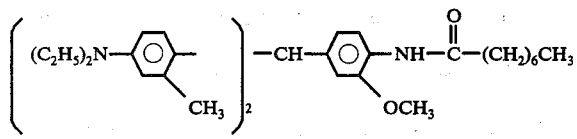

8. The photosensitive, image-forming composition mixture of claim 7 wherein said compound (1) of claim 1 has the formula

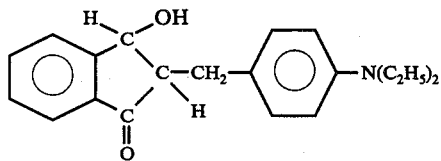

9. An article comprising an inert substrate coated with a composition of claim 8.

10. A paper substrate coated with the composition of claim 8.

11. A photosensitive, image-forming composition containing a leuco dye mixture of a compound of the general formula:

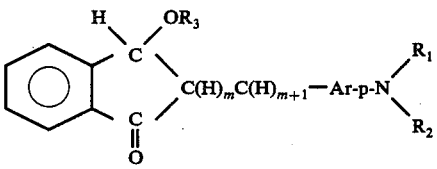

wherein $m = 1$;
Ar is phenylene;
$R_1$ and $R_2$, which may be the same or different, are lower alkyl or hydroxyalkyl groups, or

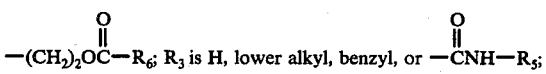

$R_5$ is H, a $C_3$-$C_6$ alkyl group, an aryl group,

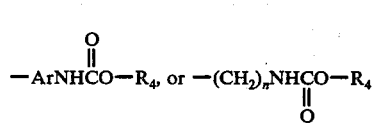

wherein $n$ = 2–6 and $R_4$ is

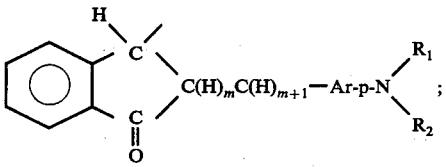

and $R_6$ is a lower alkyl group or an aryl groups, and a triarylmethane compound having the formula

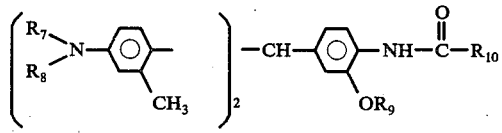

wherein $R_7$, $R_8$, $R_9$, and $R_{10}$, which may be the same or different, are lower alkyl groups, and a photooxidant capable of oxidizing the leuco dye mixture selected from the group consisting of hexaarylbiimidazole and N-halotriarylimidazole compounds.

* * * * *

UNITED STATES PATENT OFFICE
CERTIFICATE OF CORRECTION

Patent No. 4,078,934    Dated March 14, 1978

Inventor(s) John Fred Neumer

It is certified that error appears in the above-identified patent and that said Letters Patent are hereby corrected as shown below:

Column 3, line 24, " -3-nitrobenzyloxy-1-" should be -- -3-p-nitrobenzyloxy-1- --.

Column 3, line 49, after " -N-ethylaminophenyl," insert -- p-N-methyl-N-n-propylaminophenyl --.

Column 5, line 59, "hexarry" should be -- hexaaryl --.

Column 8, line 2, "haogen" should be -- halogen --.

Column 8, line 47, "ae" should be -- are --.

Column 9, line 62 "N-halophines" should be -- halolophines --.

Column 10, line 11, "on" should be -- to --.

Column 10, line 18, "1,6" should -- 1.6 --.

Column 10, line 47, "Systhesis" should be -- Synthesis --.

Column 11, line 62 "from" second occurrence should be -- form --.

Column 16, line 11, "0.330" should be -- 0.3330 --.

UNITED STATES PATENT OFFICE
CERTIFICATE OF CORRECTION

PATENT NO. : 4,078,934
DATED : March 14, 1978
INVENTOR(S) : JOHN FRED NEUMER

It is certified that error appears in the above–identified patent and that said Letters Patent are hereby corrected as shown below:

| PATENT Column | Line | |
|---|---|---|
| 19 | 29 | "Halotriarvlimidazoles" should be -- Halotriarylimidazoles --. |
| 19 | 52 | "tilted" should be -- titled --. |
| 20 | 5 | "tilted" should be -- titled --. |
| 20 | 24 | "solvent" should be -- solvents --. |
| 20 | 25 | "resonable" should -- reasonable --. |
| 20 | 34 | "tilted" should be -- titled --. |
| 23 | 16 | before "of" delete "mixture". |
| 23 | 29 | before "of" delete "mixture". |

Signed and Sealed this

Third Day of October 1978

[SEAL]

Attest:

RUTH C. MASON
Attesting Officer

DONALD W. BANNER
Commissioner of Patents and Trademarks